United States Patent
Raghuwanshi et al.

(10) Patent No.: US 10,544,408 B2
(45) Date of Patent: Jan. 28, 2020

(54) PURIFICATION PROCESS FOR ISOLATION AND COMMERCIAL PRODUCTION OF RECOMBINANT TNK-TPA TENECTEPLASE

(71) Applicant: GENNOVA BIOPHARMACEUTICALS LIMITED, Hinjwadi, Pune (IN)

(72) Inventors: Arjun Raghuwanshi, Maharashtra (IN); Shrawan Singh Kumar, Maharashtra (IN); Ankit Kumar, Maharashtra (IN); Mihir Sahoo Ranjan, Maharashtra (IN); Sanjay Singh, Maharashtra (IN)

(73) Assignee: GENNOVA BIOPHARMACEUTICALS LIMITED, Hinjwadi, Pune (IN)

( * ) Notice: Subject to any disclaimer, the term of this patent is extended or adjusted under 35 U.S.C. 154(b) by 214 days.

(21) Appl. No.: 15/505,837

(22) PCT Filed: Oct. 19, 2015

(86) PCT No.: PCT/IN2015/050137
§ 371 (c)(1),
(2) Date: Feb. 22, 2017

(87) PCT Pub. No.: WO2016/063299
PCT Pub. Date: Apr. 28, 2016

(65) Prior Publication Data
US 2018/0223270 A1     Aug. 9, 2018

(30) Foreign Application Priority Data

Oct. 21, 2014   (IN) .......................... 2343/MUM/2014

(51) Int. Cl.
*C12N 9/72*     (2006.01)
*A61K 38/48*     (2006.01)
(Continued)

(52) U.S. Cl.
CPC .......... *C12N 9/6459* (2013.01); *A61K 38/482* (2013.01); *A61K 47/02* (2013.01);
(Continued)

(58) Field of Classification Search
None
See application file for complete search history.

(56) References Cited

U.S. PATENT DOCUMENTS

2007/0014779 A1*   1/2007   Semba ............. C12Y 304/2106
                                                  424/94.63
2009/0047251 A1*   2/2009   Eichner .................. A61K 47/50
                                                  424/85.7

(Continued)

FOREIGN PATENT DOCUMENTS

WO    WO-2011/015922 A1    2/2011
WO    WO-2012/066569 A1    5/2012

OTHER PUBLICATIONS

International Searching Authority, "International Search Report," issued in connection with International Patent Application No. PCT/IN2015/050137, dated Mar. 21, 2016.
(Continued)

*Primary Examiner* — Krishnan S Menon
(74) *Attorney, Agent, or Firm* — Foley & Lardner LLP

(57) ABSTRACT

The present invention relates to a novel process of isolating and purifying tissue plasminogen activator and its variants more specifically TNK-tPA from CHO cells and describes an industrially applicable, simple, cost effective, robust and highly efficient process of TNK-tPA purification.

17 Claims, 16 Drawing Sheets

Lane Description:

1: Molecular Marker
2. Empty
3: Load
4: FT
5: Wash 1
6: Wash 2
7: Wash 3
8: Empty
9: Elution
10: Empty

(51) Int. Cl.
  *A61K 47/02* (2006.01)
  *A61K 47/18* (2017.01)
  *A61K 47/26* (2006.01)
(52) U.S. Cl.
  CPC ............ *A61K 47/183* (2013.01); *A61K 47/26* (2013.01); *C12Y 304/21068* (2013.01)

(56) References Cited

U.S. PATENT DOCUMENTS

2011/0081679 A1* 4/2011 Jing .................. C07K 14/47
  435/69.1
2013/0323227 A1* 12/2013 Mishra ................ A61K 9/0019
  424/94.64

OTHER PUBLICATIONS

International Searching Authority, "Written Opinion," issued in connection with International Patent Application No. PCT/IN2015/050137, dated Mar. 21, 2016.

Behrouz, Reza, "Intravenous tenecteplase in acute ischemic stroke: an updated review," Journal of Neurology, vol. 261, Issue 6, 2014, pp. 1069-1072.

Sanchez et al., "Design of a recombinant tissue plasminogen activator production plant," Biotechnology Final Project, 2013.

Abstract of: Staby et al., "Comparison of chromatographic ion-exchange resins V. Strong and weak cation-exchange resins," Journal of ChromatographyA, vol. 1118, No. 2, Jun. 23, 2006, pp. 168-179.

* cited by examiner

PURIFICATION PROCESS FOR ISOLATION AND COMMERCIAL PRODUCTION OF RECOMBINANT TNK-TPA TENECTEPLASE

CROSS-REFERENCE TO RELATED APPLICATIONS

The present application is a U.S. National Phase Application of International Patent Application No. PCT/IN2015/050137, filed Oct. 19, 2015, which claims priority to Indian Patent Application No. 2343/MUM/2014, filed Oct. 21, 2014, the entireties of which are incorporated herein by reference.

FIELD OF THE INVENTION

Present invention is related to a novel process of isolation, purification and production of tissue plasminogen activator (TNK-tPA) from mammalian cells, more specifically from Chinese Hamster Ovary (CHO) cells.

BACKGROUND OF THE INVENTION

Tenecteplase (TNK-tPA) is a recombinant glycoprotein of serine protease family with six amino acids substitution in the native human tissue plasminogen activator (t-PA) with 17 disulphide bridges and having molecular weight of ~67 kDa. In the development of TNK-tPA, the modifications made in native t-PA includes substitution of threonine 103 with asparagine, substitution of asparagine 117 with glutamine both within the kringle 1 domain, and the substitution of lysine, histidine and two arginine with tetra-alanine amino acids at 296-299 positions in the protease domain to make the resulting protein highly fibrin specific with longer plasma half life and 80% decreased susceptibility to degradation by plasminogen activator inhibitor-1 (PAI-1) compared to native t-PA.

The TNK in TNK-TPA refers to the sites of the t-PA molecule that have been modified i.e. T103; Ni 17; and KHRR 296-299. The aforementioned modifications of TNK-tPA renders its use as an improved therapeutic agent for the treatment of acute myocardial infarction which has better therapeutic compliance because the greater fibrin specificity allows for faster and complete clot lysis with decreased bleeding complications and the long life-span permits a single bolus dose with less systemic fibrinolysis and lesser bleeding complications from the previous clot buster drugs.

The mechanism of TNK-tPA is initiated on binding of TNK-tPA to the fibrin component of the thrombus (blood clot) which selectively converts inactive plasminogen into plasmin and consequently the resultant plasmin degrades the matrix of thrombus in occluded artery while conserving fibrinogen and minimizing systemic plasminogen activation due to its highly specific nature.

The benefits of TNK-tPA seen in myocardial infarction patients and the encouraging results from animal studies in the context of Acute Ischemic Stroke (AIS), suggested that TNK-tPA might prove to be a safer and more effective therapy than alteplase, the only drug approved by USFDA for AIS. Over the past few years, several clinical trials evaluated the use of TNK-tPA in AIS and proved that TNK-tPA has a better pharmacological profile than alteplase and also suggested that it could be an effective and safe therapeutic option in treating AIS in patients reporting within 4.5 h after symptom onset. Recently, TNK-tPA has been considered for the treatment of patients with pulmonary embolism and several clinical trials showed promising outcomes. A large number of clinical trials are still being conducted to assess the complete conclusive picture of TNK-tPA in several indications.

In the last few years, development and manufacturing of recombinant glycoproteins was carried out by batch, fed batch, semi-fed batch and perfusion bioreactors processes and for purification of these proteins adsorption and ion exchange chromatography were majorly employed.

For t-PA and its variants certain purification protocols are known in prior art e.g. purification by immuno affinity (anti-tPA goat polyclonal antibody), ion exchange, ethanol precipitation, reverse phase chromatography, chromatography on silica or anion exchange, such as diethylamino ethyl, ammonium sulphate precipitation, sephadex-G-75 etc.

Some of the approaches for the purification of TNK t-PA is listed in prior art includes WO 2011/015922, sets out a purification process where series of ion exchange chromatography steps, immunoaffinity chromatography and ultrafiltration/diafiltration steps are used for purification of TNK-tPA. WO 2012/066569 A, sets out a purification process primarily drawn to the use of hydrophobic interaction chromatography.

The immune affinity chromatography used in the prior art is not suitable technique for commercial manufacturing of TNK-EPA. Not only it could raise lot of regulatory concerns but the cost of immune affinity chromatography media is also very high compared to conventional chromatography matrices owing to their use of monoclonal antibodies for preparation. Hydrophobic interaction chromatography described in certain prior art for TNK-tPA purification uses isopropyl alcohol (IPA) in the process which is an organic solvent and known for inducing aggregation and denaturation of proteins and may be considered as one of the disadvantages of the prior art. TNK-tPA is a highly unstable molecule and hence use of IPA in the purification process should be avoided as it may lead to the denaturation of the protein. In addition, the large volume usage of IPA at commercial scale, would require recycling of IPA which regain demands additional energy consumption and extra investment such as solvent recovery unit.

Therefore, none of the aforementioned processes are capable of providing an efficient, scalable and robust purification solution, which could consistently produce TNK-tPA drug substance at commercial scale, meeting all the required specifications.

Hence, there is a need for an effective and commercially viable process for purification of TNK-tPA.

OBJECT OF THE INVENTION

The object of the present invention is to develop an efficient, robust, scalable, and commercially viable purification process for the production of TNK-tPA resulting yield not less than 60% and purity more than 95% as measured by Size exclusion chromatography.

SUMMARY OF THE INVENTION

The present invention relates to a novel process of isolating and purifying tissue plasminogen activator and its variants more specifically TNK-tPA from CHO cells and describes an industrially applicable, simple, cost effective, robust and highly efficient process of TNK-tPA purification.

A process for isolation and purification of TNK-tPA of the present invention comprising steps of:
  i) subjecting cell free harvest obtained from CHO cell culture to affinity chromatography to capture TNK-tPA and obtaining an eluate containing partially purified TNK-tPA.
  (ii) subjecting the eluate of step (i) to affinity chromatography for additional purification of TNK-tPA and obtain an eluate containing primarily TNK-tPA.
  (iii) viral inactivation of eluate of step (ii) to obtain the viral inactivated sample;
  (iv) subjecting the viral inactivated sample of step (iii) to a further affinity chromatography for additional purification to obtain an eluate containing primarily highly purified TNK-tPA;
  (v) subjecting the eluate of step (iv) to cation exchange chromatography to obtain an eluate containing highly purified preparation of TNK-tPA;
  (vi) subjecting the eluate of step (v) to virus reduction filtration for removal of virus present;
  (vii) concentrating the sample of step (vi) to obtain TNK-tPA; wherein the yield of the process is more than 60% and purity of TNK-tPA obtained is more than 95% as measured by Size exclusion chromatography.

DETAILED DESCRIPTION OF INVENTION

Figure 1:
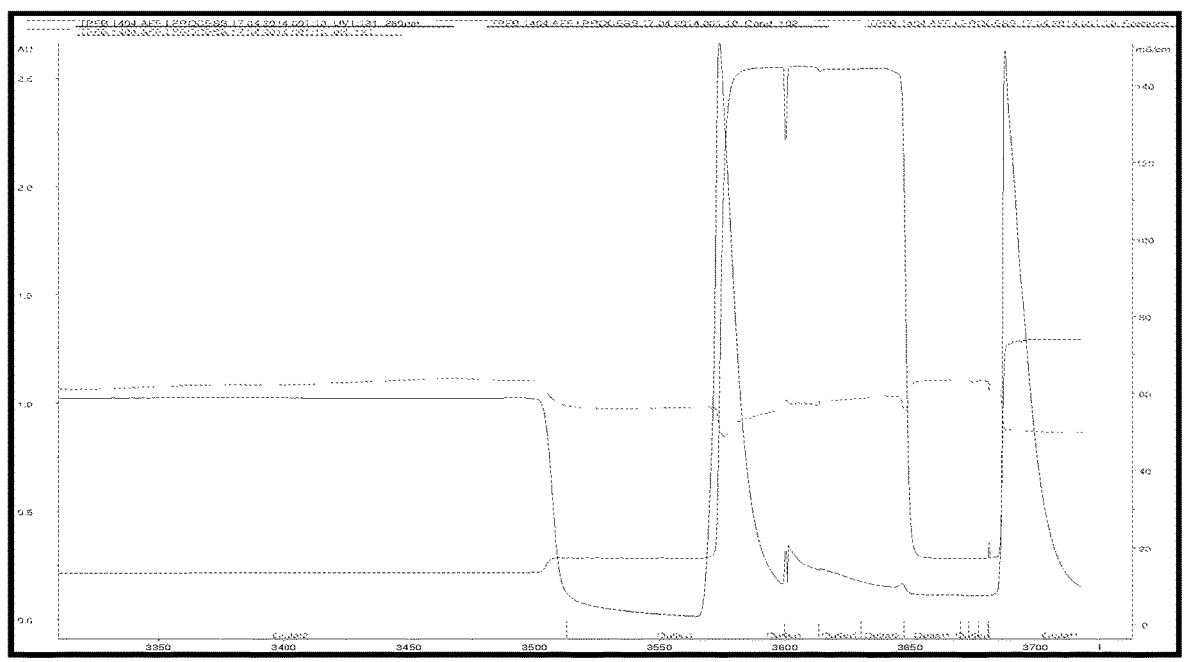
FIG. 1: Depicts a chromatogram of affinity-I purification where first peak represents impurities and second peak corresponds to eluate containing TNK-tPA.
Figure 2:
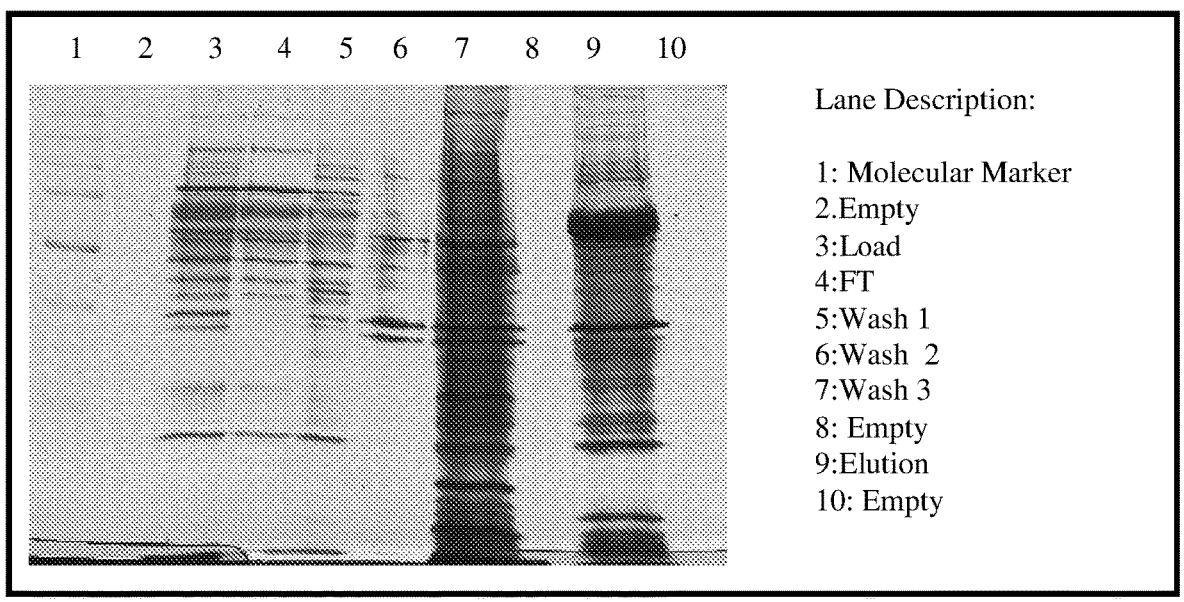
FIG. 2: Depicts a SDS PAGE (silver stained) profile of affinity-I purification where lane no 5, 6 and 7 showing wash fractions (1, 2 and 3 respectively) and Lane No. 9 corresponds to eluate containing TNK-tPA.
Figure 3:
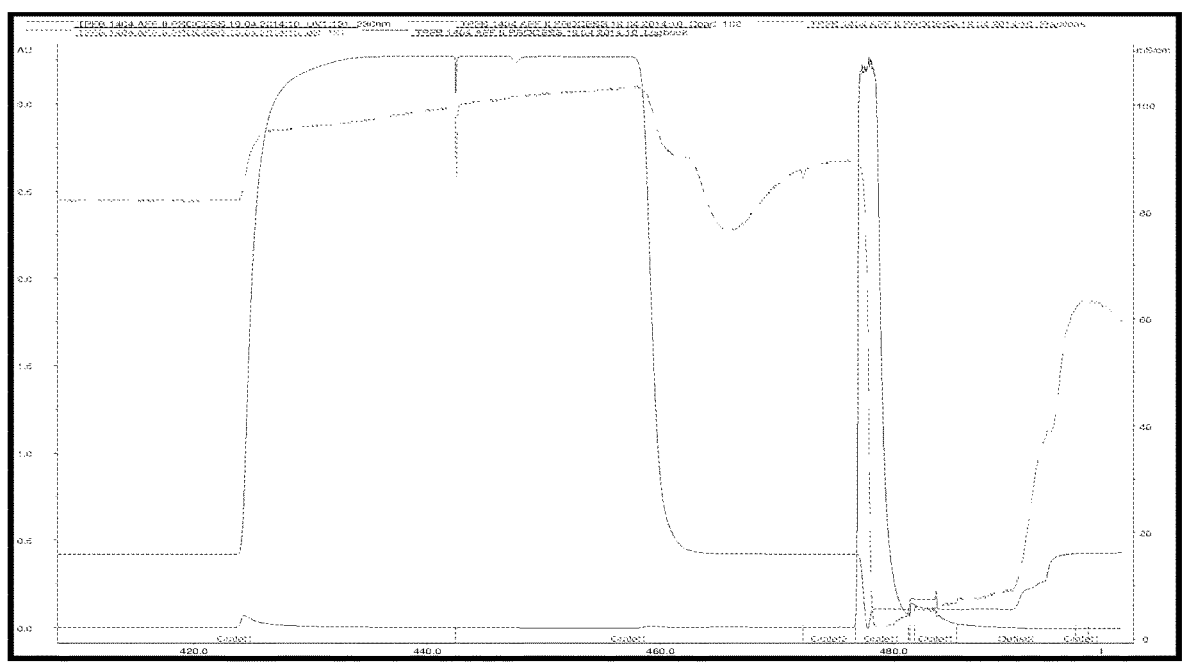
FIG. 3: Depicts a chromatogram of affinity-II purification, UV 280 peak corresponding to eluate containing TNK-tPA.
Figure 4:
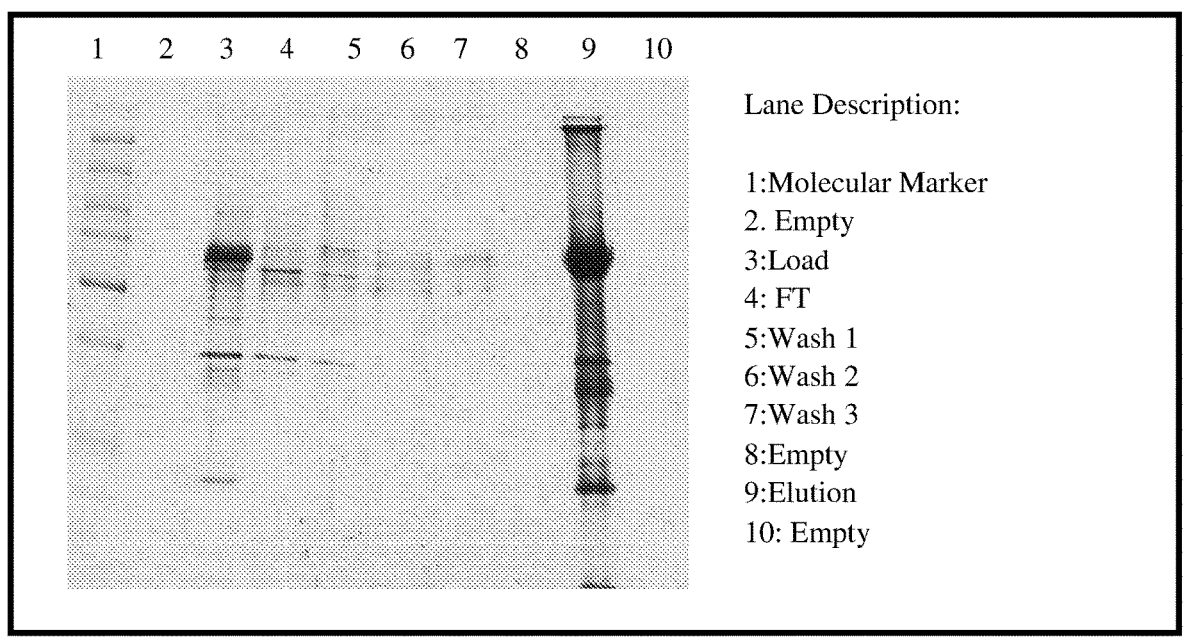
FIG. 4: Depicts a SDS PAGE (silver stained) profile of affinity-II purification where lane No. 9 corresponds to eluate containing TNK-tPA
Figure 5:
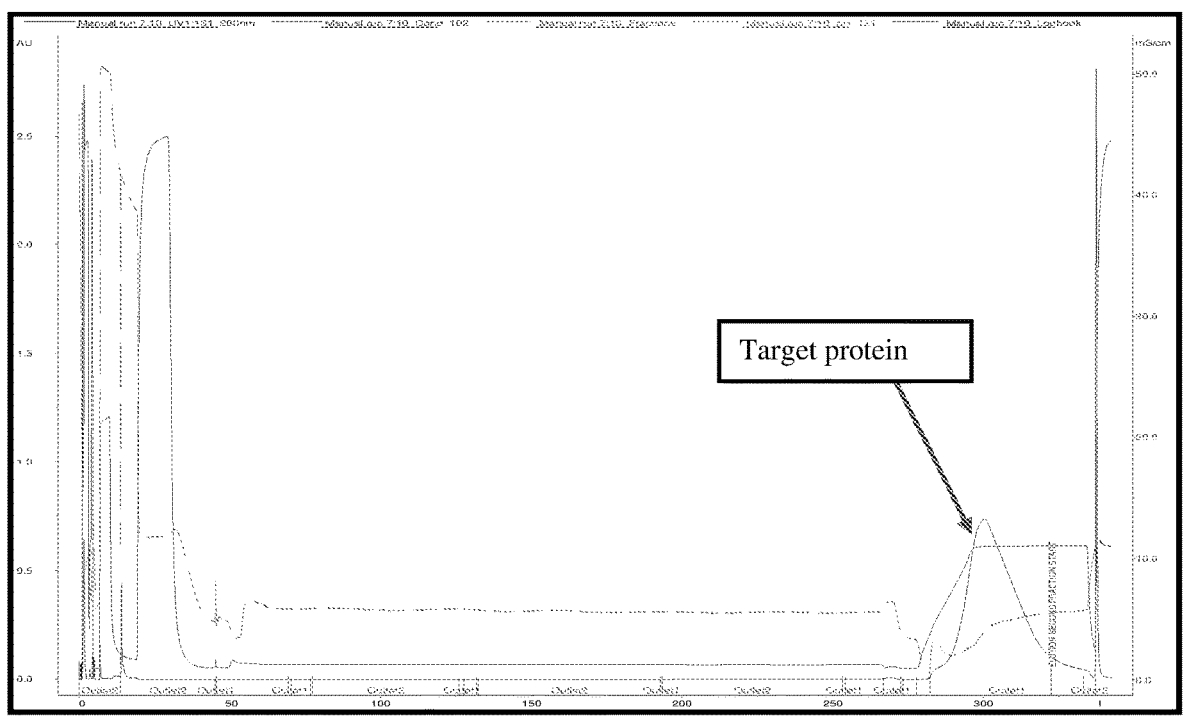
FIG. 5: Depicts a chromatogram of affinity-III purification, UV 280 peak (first) corresponds to eluate containing TNK-tPA
Figure 6:
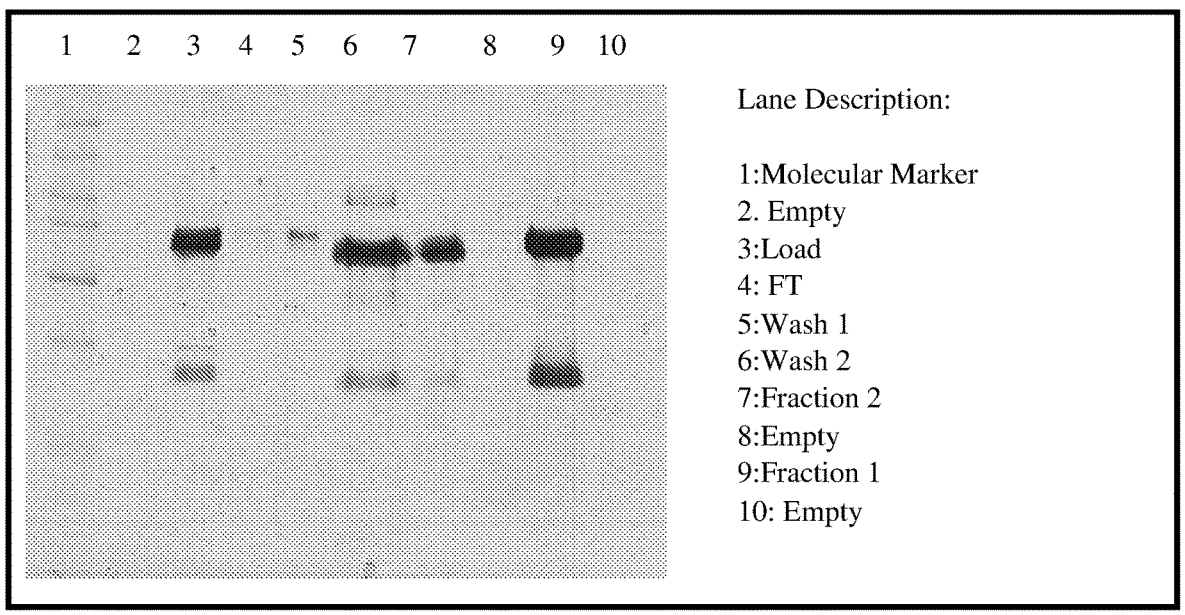
FIG. 6: Depicts a SDS PAGE (silver stained) profile of affinity-III purification where lane No. 9 corresponds to eluate containing TNK-tPA
Figure 7:
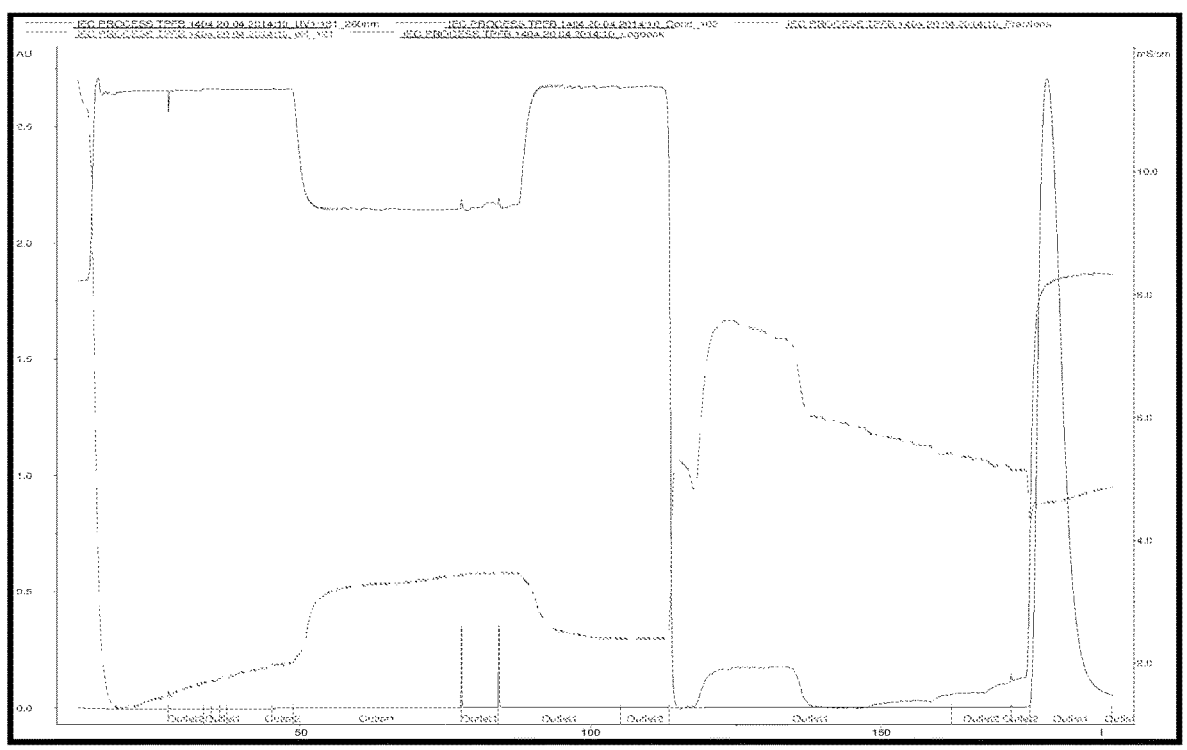
FIG. 7: Depicts a chromatogram of cation exchange purification, UV 280 peak corresponds to eluate containing TNK-tPA.
Figure 8:
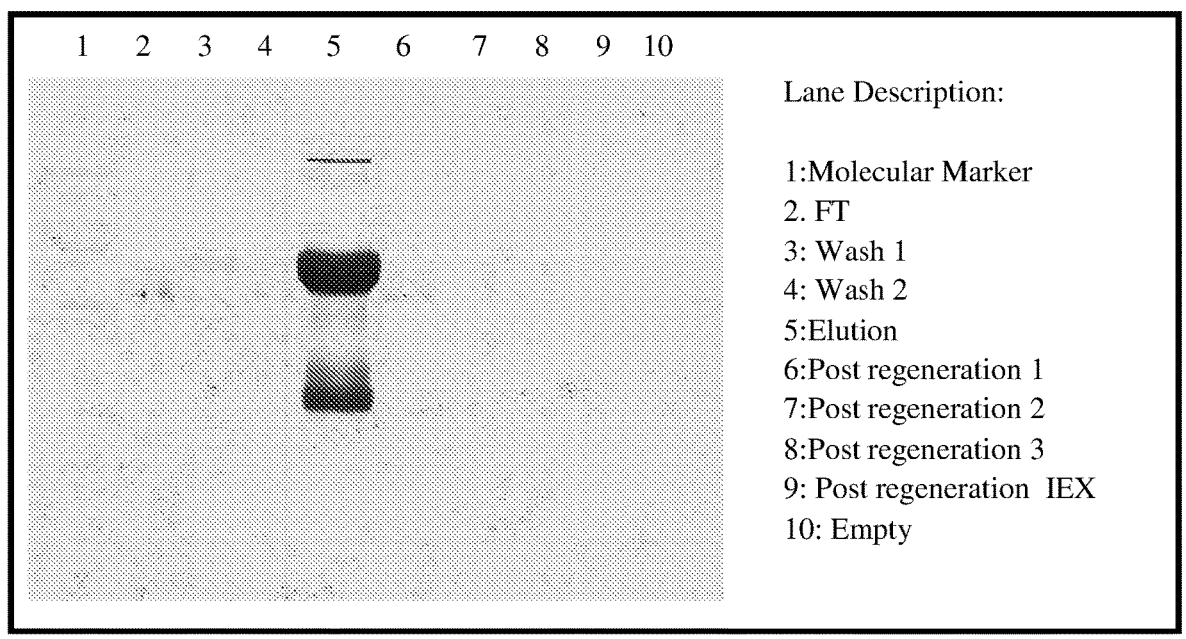
FIG. 8: Depicts a SDS PAGE (silver stained) profile of cation exchange purification where lane No. 5 corresponds to eluate containing TNK-tPA.
Figure 9:
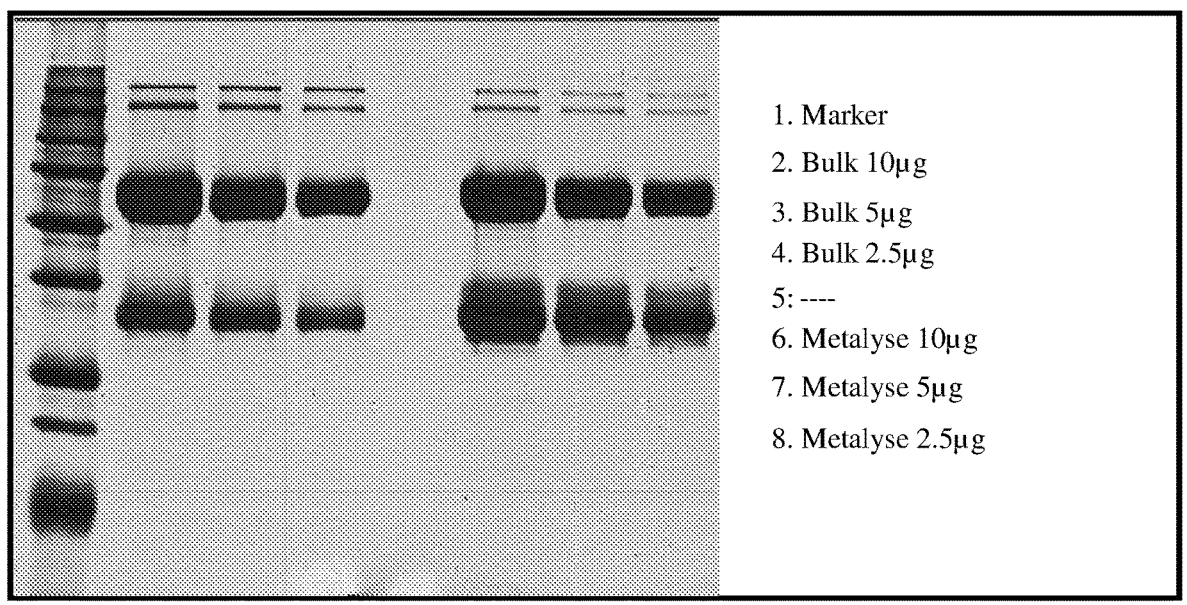
FIG. 9: Depicts a comparison of reducing SDS-PAGE (silver stained) profile of drug substance obtained after purification using steps described in present invention and innovator product (Metalyse).
Figure 10:
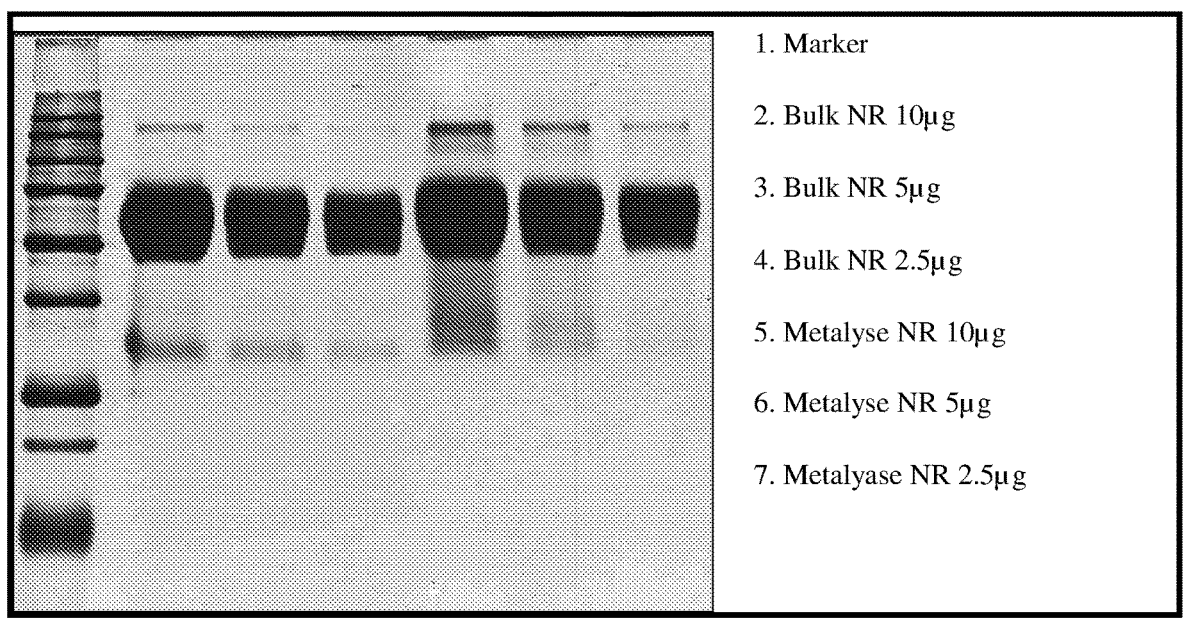
FIG. 10: Depicts a comparison of non reducing SDS PAGE (silver stained) profile of drug substance obtained after purification using steps described in present invention and innovator product (Metalyse).
Figure 11:
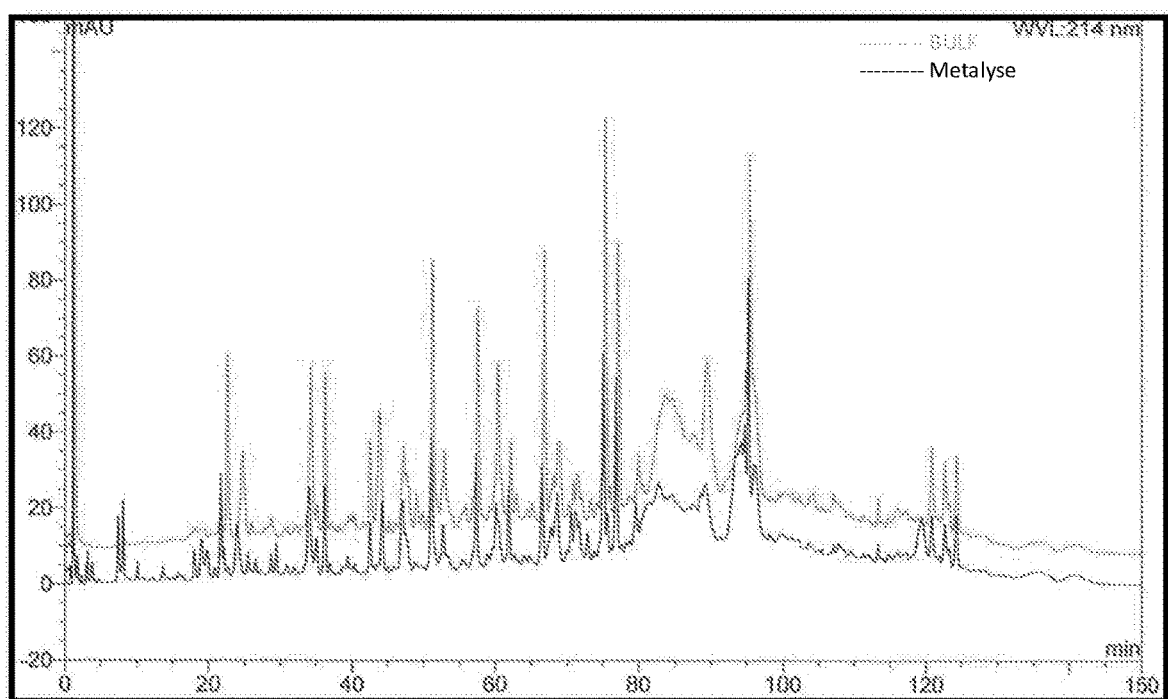
FIG. 11: Depicts a peptide map chromatogram of drug substance obtained after purification using step described in present invention resembles with innovator product (Metalyse)
Figure 12:
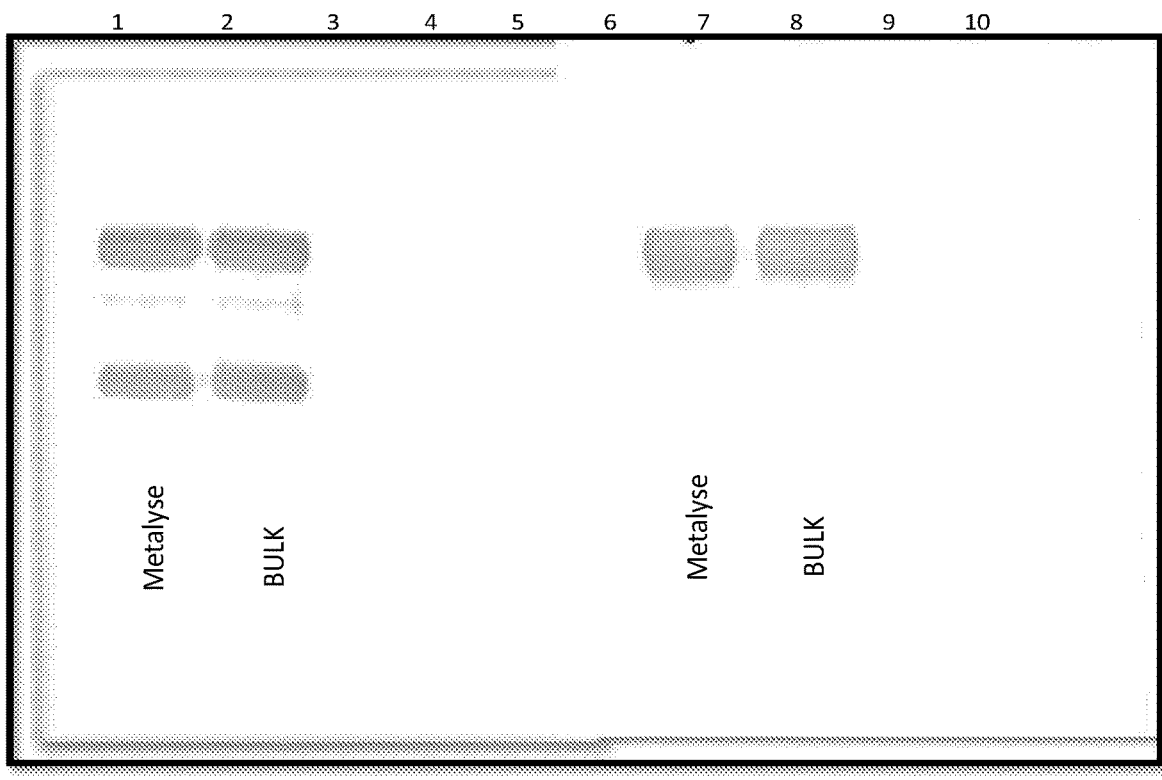
FIG. 12: Depicts a immune blotting of drug substance obtained after purification using steps described in present invention resembles with innovator product (Metalyse)
Figure 13:
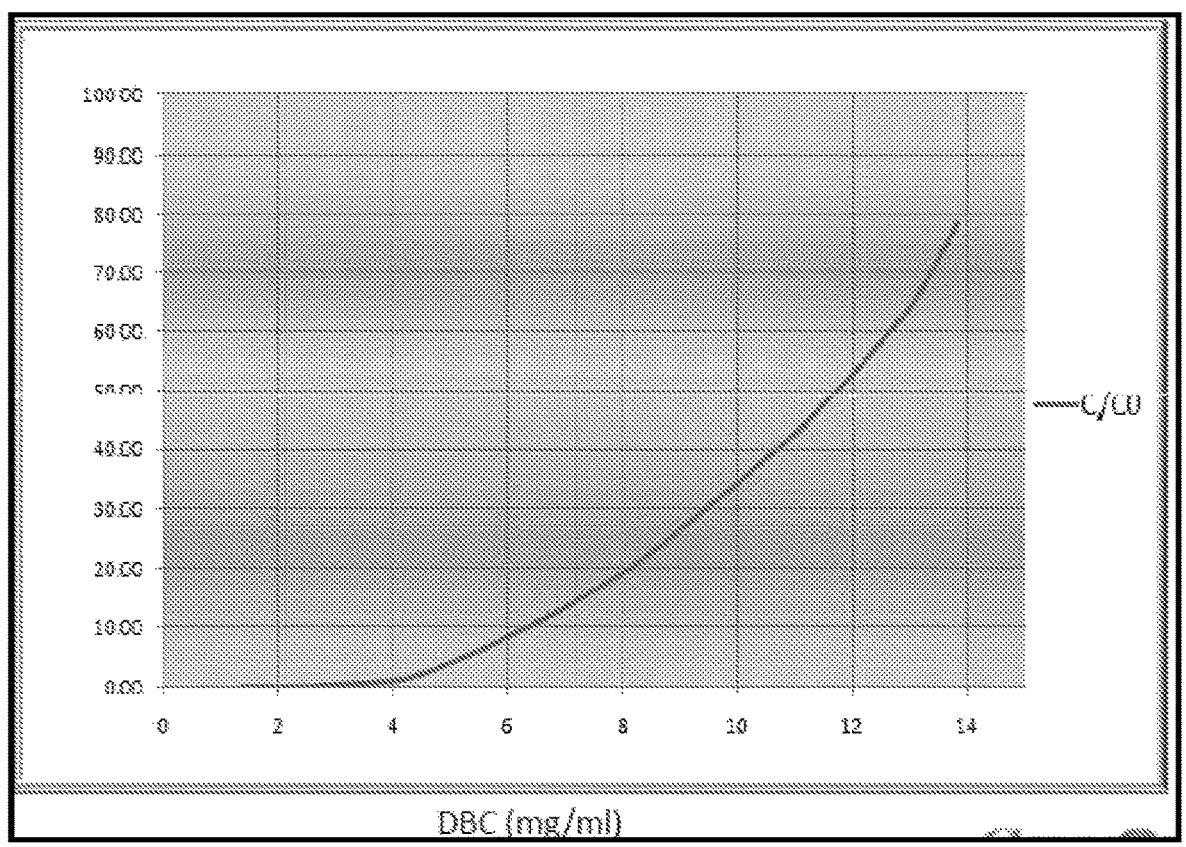
FIG. 13: Depicts the breakthrough curve of Affinity-I (Blue Sepahrose FF) in batch mode.
Figure 14:
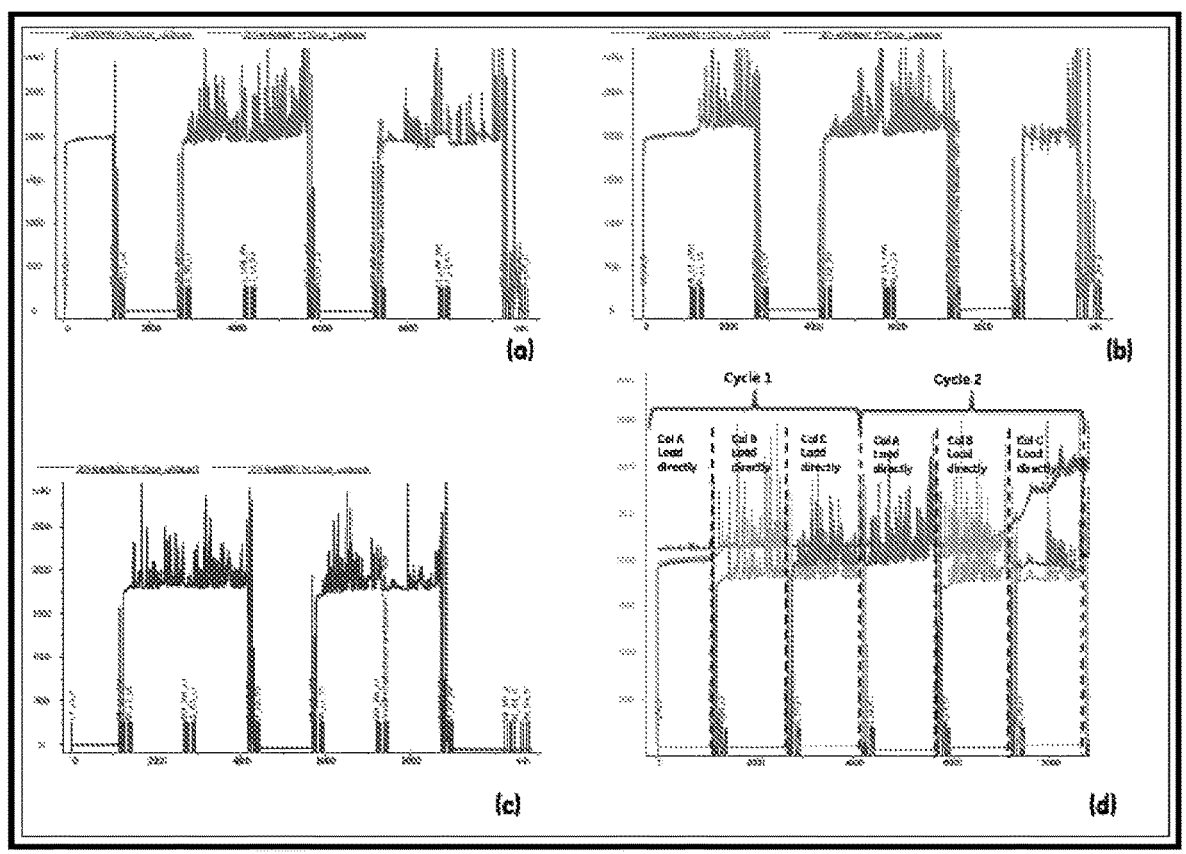
FIG. 14: Depicts Chromatograms for the PCC run over two cycles for (a) Column A—first column in the loading zone; (b) Column B—the second column in the loading zone; (c) Column C—the third column in the loading zone; (d) Column chromatograms superimposed on each other showing full PCC run. UV is measured at 280 nm. Run performed on an XK16-5 ml Blue Sepharose Fast Flow.
Figure 15:
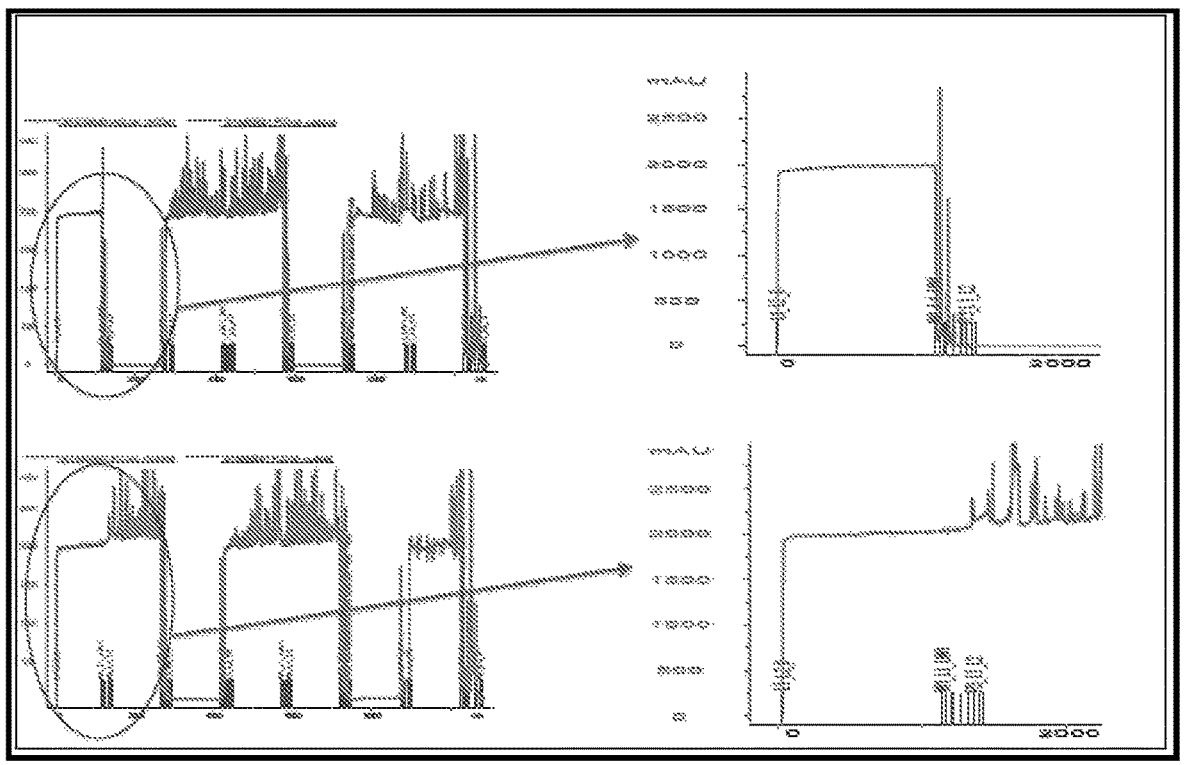
FIG. 15: Depicts Chromatogram from the first column (Column A) overloading and capture in Column B, UV measured at 280 nm. Run performed on an XK16-5 ml Blue Sepharose Fast Flow.
Figure 16:
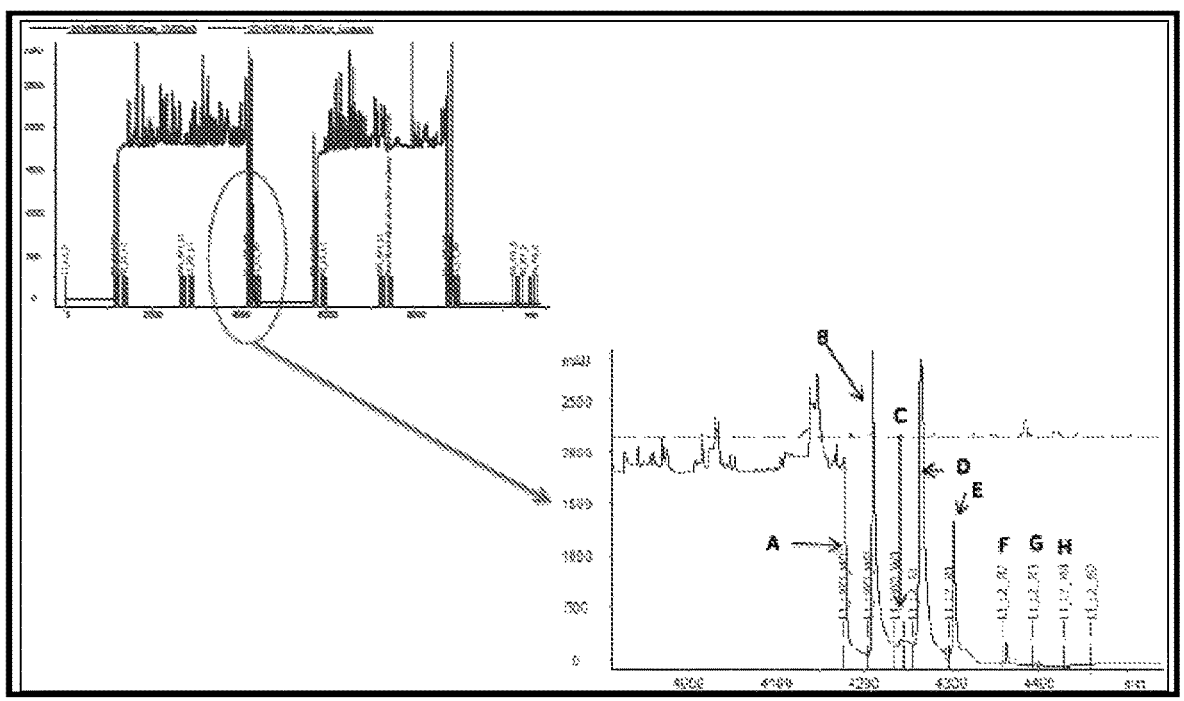
FIG. 16: Depicts Chromatogram from the third column (Column C) showing all post load washing. Impact of wash steps are denoted by A—Wash 1, B—Wash 2, C—wash 3, D—Elution, E—Regeneration 1, F—Regeneration 2, G—Regeneration 3, H—Regeneration 4. UV measured at 280 nm. Run performed on an XK16-5 ml Blue Sepharose Fast Flow.

The present invention relates to a novel process of isolating and purifying tissue plasminogen activator and its variants more specifically TNK-tPA. The cell free harvest is obtained from the cells cultured in bioreactors. The list of symbols and abbreviations used in specification of the present invention are listed at Table A below:

TABLE A

| \multicolumn{2}{c}{List of symbols and abbreviations} | |
|---|---|
| tPA | Tissue Plasminogen Activator |
| CHO | Chinese Hamster Ovary |
| kDa | Kilo-Dalton |
| PAI | Plasminogen Activator Inhibitor |
| AIS | Acute Ischemic Stroke |
| SDS PAGE | Sodium Dodecyl Sulfate Polyacrylamide Gel Electrophoresis |
| IPA | Isopropyl Alcohol |
| CHT | Ceramic Hydroxy Apatite |
| FF | Fast Flow |
| mM | Milli Molar |
| MTX | Methotrexate |
| EACA | Epsilon-aminocaproic acid |
| MES-Hydrate | 2-(N-Morpholino) ethanesulfonic acid hydrate |
| TFF | Tangential Flow Filtration |
| UF | Ultrafiltration |
| DF | Diafiltration |
| PES | Polyethersulphone |
| PVDF | Polyvinylidene Fluoride |
| μ | Micron or Micrometer |
| XMuLV | Xenotropic Murine Leukemia Virus |
| PRV | Pseudorabies Virus |
| Reo-3 | Reovirus Type 3 |
| MMV | Murine Minute Virus |
| CV | Column Volume |
| DBC | Dynamic Binding Capacity |
| HCP | Host Cell Protein |
| DNA | De-oxyribo Nucleic Acid |
| HCD | Host Cell DNA |
| SEC-HPLC | Size Exclusion Chromatography |
| HPLC | High Performance Liquid Chromatography |
| LAL | Limulous Amoebocyte Lysate |
| UV | Ultraviolet |
| MMC | Mixed Mode Chromatography |

The present invention relates to a novel process of isolating and purifying tissue plasminogen activator and its variants more specifically TNK-tPA from CHO cells and describes an industrially applicable, simple, cost effective, robust and highly efficient process of TNK-tPA purification A process for isolation and purification of TNK-tPA of the present invention comprising steps of:
  i) subjecting cell free harvest obtained from CHO cell culture to affinity chromatography to capture TNK-tPA and obtaining an eluate containing partially purified TNK-tPA.
  (ii) subjecting the eluate of step (i) to affinity chromatography for additional purification of TNK-tPA and obtain an eluate containing primarily TNK-tPA.
  (iii) viral inactivation of eluate of step (ii) to obtain the viral inactivated sample;
  (iv) subjecting the viral inactivated sample of step (iii) to a further affinity chromatography for additional purification to obtain an eluate containing primarily highly purified TNK-tPA;
  (v) subjecting the eluate of step (iv) to cation exchange chromatography to obtain an eluate containing highly purified preparation of TNK-tPA;
  (vi) subjecting the eluate of step (v) to virus reduction filtration for removal of virus present;
  (vii) concentrating the sample of step (vi) to obtain TNK-tPA; wherein the yield of the process is more than 60% and purity of TNK-tPA obtained is more than 95% as measured by Size exclusion chromatography.

The process of the present invention may be explained by illustrating the steps as below:
  (i) Subjecting cell free harvest obtained from CHO cell culture to affinity chromatography to capture TNK-tPA and obtaining an eluate containing partially purified TNK-tPA.
    The cell free harvest containing TNK-tPA may be obtained from perfusion technology based fermentation system by CHO cells. The harvest containing TNK-tPA may be filtered with 0.2μ and collected in sterile containers and stored at 2-8° C. till further use. The cell free harvest containing TNK-tPA is subjected to affinity chromatography. The stationary phase of affinity chromatography may be selected from the group comprising Blue Sepharose 6 fast flow, Lysine Hyper D, Ceramic Hydroxy Apatite (CHT), preferably the stationary phase is Blue Sepharose 6 FF. The column may be equilibrated by using a buffer comprising Phosphate buffer, sodium chloride and polysorbate 20 or their mixtures. The elution buffer or mobile phase employed for capture step (Affinity Chromatography) may be individually or in combination selected from phosphate buffer, urea, and sodium chloride. More preferably, the elution buffer or mobile phase is used in combination. The concentration of sodium phosphate in buffer used is preferably 20-50 mM sodium phosphate, more preferably 20-40 mM. The concentration of sodium chloride used in the buffer is 1-2.5 M NaCl, more preferably 1.5-2M. The concentration of urea in the buffer may be in the range of 1-4 molar, preferably in the range of 2-3 molar. The pH of the elution buffer or mobile phase may be maintained in the range of 7-8, preferably in the range of 7-7.6, more preferably in the range of 7.2-7.4.
    The removal of host cell proteins from products produced in mammalian cells is always a difficult task. In the present invention the step optimized as capture chromatography in current invention selectively removes host cell proteins to an extent of 0.8 to 1.5 log, more specifically 1.0 log which helps in achieving final concentration of HCP in purified TNK-tPA preparation, below 100 ppm.
    Not only the host cell proteins (HCP) are reduced but process related impurities such as albumin, gentamycin, Methotrexate (MTX) etc. are also removed effectively by the capture chromatography described in present invention.
  (ii) Subjecting the eluate of step (i) to affinity chromatography for additional purification of TNK-tPA to obtain an eluate containing primarily TNK-tPA.
    The eluate of step (i) may be subjected to affinity chromatography. The stationary phase or column material may be selected from the group comprising of Blue Sepharose 6 fast flow, Lysine Hyper D, Ceramic Hydroxy Apatite (CHT), etc., preferably the stationary phase is Lysine Hyper D. The equilibration buffer employed in Affinity chromatography step may be individually or in combination selected from Phosphate buffer, sodium chloride and polysorbate. More preferably the equilibration buffer is used in combination.
    The column may be eluted by a elution buffer or mobile phase selected from the group comprising individually or in combination selected from sodium acetate, urea and Epsilon-aminocaproic acid (EACA). The pH of the affinity chromatography elution buffer may be done in the range of pH 3.5-6, preferably 4-5, more preferably 4.5-5.
    The chromatography matrix employed for intermediate purification e.g. Affinity-II chromatography step may be selected from the group comprising of Blue Sepharose 6 fast flow, Lysine Hyper D and Ceramic Hydroxy Apatite (CHT), preferably the chromatography matrix used is Lysine Hyper D.
    The elution buffer employed in Affinity chromatography step may be 5-25 mM sodium acetate, 1-4 M urea, 0.1-0.4 M EACA having pH 4.0-5.0. The concentration of sodium acetate in elution buffer is 5-25 mM, preferably in the range of 5-15 mM. The concentration of EACA in the buffer is 0.1-0.4 mM, preferably in the range of 0.1-0.2 M. The concentration of urea is 1-4 M in the buffer, preferably in the range of 2-3 M.
    The inventive merit of elution buffer by using EACA at acidic pH in this step is to provide the most suitable condition. The process of the present invention as set out herein is most suitable for viral inactivation and reduces the handling and material consumption by several folds. Approximately 2-4 log reduction of viral clearance and 1-1.5 log reduction of host cell proteins (HCP) are achieved by Affinity chromatography used in present invention. On an average the 1.69 log reduction with XMuLV and 4.30 log reduction with PRV are achieved by Affinity chromatography used in present invention.
  (iii) Viral inactivation of eluate of step (ii) to obtain the viral inactivated sample;
    The viral inactivation of the eluate obtain from step (ii) may be conducted by any method such as heat treatment (Pasteurization, Lyophilisation/dry heat), irradiation, ultraviolet (UV), high hydrostatic pressure, low pH incubation, chemical and solvent/detergent treatments. Chemical inactivation or viral inactivation is done by treating the sample with chemical selected from the group comprising sodium cholate, triton, Beta-propiolactone, tri(n-butyl)phosphate (TNBP), and sodium caprylate, preferably treating the sample with sodium caprylate at low pH in the presence of Urea. The concentration of chemical/detergent is in the range of 0.001% to 0.10% w/v, preferably 0.01%-0.07% (w/v), more preferably 0.05%. The concentration of urea is used in the range of 1-4 M, preferably 2-3 M. The viral activation may also be carried out by incubating the sample for a period of 40-180 minutes, more preferably for a period of 40-80 minutes, in the temperature range of 15-45° C., more preferably in the range of 20-30° C.

Generally low pH is the choice and most widely used method of viral inactivation in purification processes. Low pH is known to inactivate enveloped viruses but it cannot inactivate highly resistant non enveloped viruses. The pH is in range from 4.0 to 4.7, more preferably in range from 4.3 to 4.7.

The composition of viral inactivation buffer described in present invention is optimized in such a manner that it could inactivate both enveloped and non enveloped viruses efficiently. Use of the chemicals/detergents, urea, EACA and low pH of the present invention makes the conditions lethal for enveloped and non enveloped viruses and makes the combination an optimum choice for inactivating highly resistant viruses. On an average 5.65 log reduction with XMuLV, 5.38 log reduction with PRV are achieved by low pH and chemical inactivation of the present invention.

(iv) Subjecting the viral inactivated sample of step (iii) to a further affinity chromatography to obtain an eluate containing TNK-tPA;

The viral inactivated sample of step (iii) may be subjected to a further affinity chromatography. The stationary phase or column material of affinity chromatography may be selected from the group of Blue Sepharose 6 fast flow, Lysine Hyper D, Ceramic Hydroxy Apatite (CHT), etc., preferably the stationary phase or chromatography matrix used is Ceramic Hydroxy Apatite (CHT). The stationary phase or column may be eluted by a mobile phase or buffer selected from the group comprising individually or in combination selected from Phosphate buffer, 2-(N-Morpholino)ethanesulfonic acid hydrate (MES-Hydrate), sodium chloride and urea. The pH of the affinity chromatography elution buffer may be done at pH ranging from 6-9, preferably 6-8, more preferably 6-7.

The mobile phase or elution buffer employed in Affinity chromatography step may be 5-50 mM phosphate buffer, preferably in the range of 5-15 mM. The concentration of urea is used in the range of 1-4 M in buffer, preferably in the range of 1-3 M. The concentration of MES-Hydrate used may be 2-20 mM in the buffer. Elution may be carried by increasing concentration of salt. The salt of this elution may be selected from group of potassium chloride, sodium chloride, sodium phosphate and ammonium sulphate, preferably the salt is sodium chloride and concentration of sodium chloride is in range of 0.1-1.0 M sodium chloride. The elution type may be linear, step or in combination of both, preferably the elution used is linear salt gradient.

Affinity chromatography (multimode chromatography) used in present invention is to remove traces of impurities, specifically host cell DNA (HCD), host cell proteins (HCP) and viral impurities if any. Approximately 2-4 log reduction of viral clearance and 0.5-1 log reduction of HCP is achieved using affinity-III chromatography mentioned in current invention. On an average 4.23 log reduction with XMuLV, 4.06 log reduction with PRV, 3.73 log reduction with Reo-3 and 2.97 log reduction with MMV are achieved by Affinity chromatography used in present invention.

(v) Subjecting the eluate of step (iv) to cation exchange chromatography to obtain an eluate containing highly purified preparation of TNK-tPA in formulation buffer;

The cation exchange chromatography of the eluate of step (iv) may be conducted by using a matrix or stationary phase selected from the group comprising Fractogel $SO_3$, Fratogel SE Hicap, SP Sepharose FF, CM Sepharose FF etc., preferably the chromatography matrix or stationary phase used is Fractogel $SO_3$. The equilibration buffer employed in cation exchange chromatography may be individually or in combination selected from group comprising phosphate buffer, urea, MES and sodium chloride, preferably the equilibration buffer is used in combination.

The elution buffer or mobile phase employed in cation exchange chromatography may be individually or in combination selected from L-Arginine, O-phosphoric acid and polysorbate-20, preferably, the elution buffer is used in combination or mixture. The mobile phase or elution buffer employed in cation exchange chromatography comprising L-Arginine present in range from 10-350 mM, preferably in range from 250-350 mM, O-phosphoric acid present in range from 0.5-1%, preferably in range from 0.6%-0.8% and polysorbate-20 present in range from 0.01-0.05%, preferably in range from 0.04 to 0.05%. The pH of the cation exchange chromatography elution buffer or mobile phase may be done in the range of 7.0 to 7.5, preferably in the range 7.3-7.5.

Generally the ion exchange chromatography is used as capture, intermediate and polishing chromatography to either remove bulk or traces of impurities. In present invention the cation exchange chromatography is somewhat used differently than it is conventionally used. Herein, the eluate of previous chromatography is directly loaded on to cation exchange chromatography to obtain the highly purified preparation of TNK-tPA in final formulation buffer containing arginine, orthophosphoric acid and polysorbate 20. The advantage of using cation exchange chromatography differently is that buffer exchange and simultaneous concentration and purification are achieved in a single step. In prior art techniques like gel filtration chromatography and diafiltration using Tangential Flow Filtration (TFF) are employed for buffer exchange. These techniques are efficient and most commonly used for buffer exchange but cannot further purify target protein. Due to the fact that one can only load maximum 30% of sample to column volume in gel filtration chromatography, bigger size of columns are required compared to ion exchange chromatography. Gel filtration chromatography also causes the dilution of target protein during buffer exchange which further requires some additional concentration step like TFF. Buffer exchange using diafiltration is also not feasible when volumes to be buffer exchanged are higher since it requires very high amount of buffer and demands large size of UF/DF unit. Considering aforementioned limitations of conventional buffer exchange techniques the cation exchange chromatography described in present invention is capable to provides a buffer exchange step and assists in further purification also. It is possible to achieve a viral reduction factor of 1.21 log with non enveloped virus e.g. MMV using ion exchange chromatography of the present invention.

(vi) subjecting the eluate of step (v) to virus reduction filtration for removal of virus present;

The virus filtration may be performed after affinity chromatography, cation exchange chromatography, and tangential flow filtration step, more preferably the virus filtration step is performed after cation exchange chromatography. Nanofilter selected for this step may be of 15 nm, 20 nm, and higher. Preferably the nanofilter size is between 15-20 nm. The nanofilter used may be made up of cellulose, PES, PVDF etc. More preferably the filter used is PES.

The filtration performed after virus filtration may be selected from microfiltration, ultra filtration, nano filtration, macro filtration, tangential flow filtration, etc. More preferably the filtration is tangential flow filtration. On an average 4.15 log reduction with XMuLV, 3.40 log reduction with PRV, 4.41 log reduction with Reo-3, 4.76 log reduction with MMV are achieved by virus reduction filtration used in present invention.

The Overall downstream process provides more than 15 log reduction with XMuLV, more than 17 log reduction with PRV, more than 8 log reduction with Reo-3, and more than 8 log reduction with MMV.

The most probable contaminant in the process of TNK t-PA would be CHO cell derived retrovirus and XMuLV represents a non-defective C type retrovirus for CHO cells, a more than 15 log reduction obtained for XMuLV is considered most relevant and gives a high assurance in terms of viral safety.

(vii) Concentrating the sample of step (vi) to obtain TNK-tPA.

The filtrate obtained in step (vii) is subjected to filtration method selected from the group comprising microfiltration, ultrafiltration, nanofiltration, microfiltration and tangential flow filtration, preferably the filtration method is tangential flow filtration. Ultra filtration membrane selected for this step may be of 5, 10, 30 or 50 kDa. Preferably the ultra filtration membrane used is in the range of 5-30 kDa, more preferably the size of ultra filtration membrane used is 10 kDa. The Ultra filtration membrane used may be made up of cellulose, PES, PVDF etc. More preferably the filter used is PES. The concentration of TNK-tPA retentate may be in the range of 1.0±0.4 mg/ml to 7.0±0.4 mg/ml. More preferably, the concentration of TNK-tPA may be in the range of 1.0±0.4 mg/ml to 6.0±0.4 mg/ml. Most preferably, the concentration of TNK-tPA is 5.5±0.4 mg/ml.

The TNK-tPA drug substance (Tenecteplase) may preferably be obtained by sterile filtration of TFF Retentate using 0.2μ sterilizing grade filters made up of PES, PVDF, and Cellulose. More preferably sterile filter is made up of PES.

The present invention also discloses a process, wherein the batch Affinity-I chromatography may also be operated in continuous mode using periodic counter current chromatography (PCC). The use of PCC, provides additional advantage e.g. reduced buffer consumption, increased productivity, steady state operation and better process controls.

The present invention, includes within its scope, the use of inline buffer and chromatography load conditioning cum preparation by five pump based customized AKTA process system with a maximum flow rate of 600 L/h. The said activity can be performed by Flow feedback or pH-Flow feedback mode of control for buffer and chromatography load preparation of Affinity-I, II, III and IEC chromatography steps as mentioned in Example 1 to 4.

The process of the present invention results in a purified product of TNK-tPA with increased yield and purity. The attributes of TNK-tPA obtained by the process of the present invention is set out in detail at Table B.

TABLE B

Results pertaining to Quality of TNK-tPA

| S. No. | Critical Quality Attribute | Quality of Purified TNK-tPA BULK |
|---|---|---|
| 1 | Appearance | Clear colorless to slightly yellowish liquid |
| 2 | pH | 7.0-7.6 |
| 3 | Protein (mg/ml) | Not less than 5.0 mg/ml |
| 4 | SDS PAGE | No additional band other than principal band observed |
| 5 | Immunoblotting | Identified with specific antibody and resembles with qualified standard |
| 6 | Bioactivity (U/mg) | 160 U/mg to 240 U/mg |
| 7 | Monomer (%) | More than 95% |
| 8 | Single Chain Content (%) | More than 60% |
| 9 | HCP (ppm) | Less than 100 ppm |
| 10 | Sialic Acid (mol/mol of TPA) | 2.9 to 5.7 moles/mol of TNK-tPA |
| 11 | Neutral Sugar (mol/mol of TPA) | 10.5 to 13.5 moles/mol of TNK-tPA |
| 12 | Type I, Type II content | Type-I 28-40%, Type-II 60-72% |
| 13 | HCD | Less than 10 ng/dose |
| 14 | BET | <1 EU/mg |
| 15 | N-Terminal Sequence (First 15 amino acid) | Serine(S)-Tyrosine(Y)-Glutamine(Q)-Valine(V)-Isoleucine(I)-Cysteine(C)-Arginine(R)-Aspartic acid(D)-Glutamic acid(E)-Lysine(K)_Threonine(T)-Glutamine(Q)-Methionine(M)-Isoleucine(I)-Tyrosine(Y) |
| 16 | Osmolality | 260-320 mOsm/Kg |
| 17 | Arginine Content | 50-60 mg/ml |
| 18 | Peptide mapping | Chromatogram pattern resembles with qualified standard |
| 19 | UV Spectrum ($A_{max}$) | 280 ± 2 nm |

In an embodiment the process of the present invention is capable to remove or inactivate viruses as potential adventitious agents as assessed using a scaled down purification process. The high log clearance values obtained for XMuLV, PRV, Reo-3, and MMV provides a very good assurance that any adventitious viruses which could not be detected, or might gain access to the production process, would be cleared/or inactivated, during highly capable purification process, mentioned in the current invention and thus reducing the overall risk to patient safety.

In addition to higher assurance of viral safety, the aforementioned improvements in the purification process of TNK-tPA are also beneficial in terms of decreased human intervention, lower capital and operational expenditures for higher yield TNK-tPA preparation.

In an embodiment the present invention provides a pharmaceutical composition comprising the TNK-tPA retentate obtained from the process of present invention in liquid parenteral I.V formulation with pharmaceutically acceptable excipients for acute myocardial infarction and acute ischemic stroke.

In an embodiment the pharmaceutical composition of present invention comprises:

| Ingredient | Concentration |
|---|---|
| Tenecteplase | 5 mg |
| Arginine | 55 mg |
| Polysorbate-20 | 0.43 mg |
| Phosphoric Acid | 17 mg |
| Water for injection | q.s to 1.0 ml |

In another embodiment the present invention provides the use of the isolated and prepared TNK-tPA in liquid parenteral I.V formulation for acute myocardial infarction and acute ischemic stroke.

The invention is described in detail herein below with respect to the following examples which are provided merely for illustration and are not intended to restrict scope of invention in any manner. Any embodiments that may be apparent to a person skilled in the art are deemed to fall within the scope of present invention.

Example-1

The cell free harvest containing TNK-tPA is subjected to Affinity chromatography column packed with Blue Sepharose FF. before loading, the Column is equilibrated with 5 Column Volume (CV) of equilibration buffer. The loading is stopped till column achieve saturation. The loading capacity of column is decided based on the Dynamic Binding Capacity (DBC) of column which is in range of 1-2 mg/ml. After loading, column is washed with equilibration buffer until loosely bound process and product related impurities were washed away in equilibration wash. For further removal of host cell proteins another wash buffer is used which is composed of urea, sodium chloride, sodium phosphate and polysorbate 20.

After column wash, TNK-tPA is eluted using elution buffer containing 20-50 mM Sodium Phosphate, 1-2 M NaCl, 2-3 M urea, and 0.04-0.1% polysorbate 20. Affinity-I eluate is filtered with 0.2 μm filter. Samples are withdrawn and analysed by reduced and non reduced SDS PAGE to know the purity profile and single chain/double chain content. Those who skilled in art can understand the criticality of single chain/double chain composition in final TNK-tPA drug substance.

The present invention is advantageous due to direct capture of clarified harvest without mixing in large mixing tanks.

Example-2

Affinity-I Chromatography Eluate is diluted with affinity-II dilution or affinity chromatography equilibration buffer containing 20-50 mM Sodium Phosphate, 0.04-0.1% polysorbate20 at pH 7.2 to reduce the conductivity up to less than 15 ms/cm. Diluted sample is clarified using 0.2μ filter and loaded on to Affinity-II chromatography. Column is washed with equilibration buffer to bring the UV280 absorbance to baseline. Column is further washed to remove process and product related impurities with wash buffer containing 20-50 mM sodium phosphate, 1-3 M NaCl, 0.04-0.1% polysorbate 20 and pH 7.2. Purified TNK-tPA is recovered and eluted from the column by passing elution buffer consisting of 5-25 mM sodium acetate, 1-4 M urea, 0.1-0.4 M EACA and pH 4.0-5.0. All the chromatography samples including load, flow through, washes, and elution were analyzed using following analytical methods:

SDS PAGE (reduced/non reduced) for purity and single chain/double chain content.

Size Exclusion High Performance Chromatography (SEC-HPLC) For Aggregate Content

TNK-tPA content measured by Clot Lysis assay.

Total Protein by Bradford and UV280 nm.

HCP content using ELISA (Cygnus third generation kit)

Affinity chromatography is optimized for removing process & product related impurities. The method of elution in this step is optimized in such a way that it complements to viral inactivation step and the composition with condition of elution buffer e.g. urea, EACA, and low pH are optimized to inline with viral inactivation. Approximately 2 to 4 log reduction of viral clearance and 1.0 to 1.5 log reduction of host cell proteins (HCP) are achieved after Affinity-II chromatography step.

The other advantage is using EACA at acidic pH in Affinity Chromatography-II in elution buffer inspite of L-Arginine and EACA at neutral pH. This particular change in purification step is valuable in reducing the cost of L-Arginine and also provides an optimum condition for viral inactivation. Hence, it can be stated that the same step is not only favorable for TNK-tPA elution but also optimum for viral inactivation that in turn reduces the work load and material consumption with time.

Example-3

The Elution of Affinity Chromatography is subjected to low pH and chemical inactivation using sodium caprylate. Mixture is incubated at 20 to 25° C. for 60 min. In viral inactivation step, sodium caprylate used is in very low amount that eliminates the need of large mixing vessels. In prior art sodium caprylate was used to inactivate viruses present in before capture chromatography where volumes are comparatively higher hence quantity of sodium caprylate required was also high. In present invention, sodium Caprylate is added after second chromatography steps where volume to be handled is low and therefore requires less amount of sodium caprylate and much smaller vessel for handling. Apart from that, the use of sodium caprylate at pH 4.5 as compared to neutral or alkaline pH, provides a more effective and robust viral inactivation in the process.

After viral inactivation the solution is diluted using phosphate buffer for loading on to Affinity chromatography (mixed mode chromatography) to remove traces of impurities, specifically HCD, HCP and viral impurities if any. Approximately 2-4 log reduction of viral clearance and 0.5-1 log reduction of HCP clearance are achieved by affinity chromatography. In prior art same ceramic hydroxyl apatite is described for tissue plasminogen activator purification, but none of the process have described the capability to remove impurities e.g. HCP, DNA and viruses. Criticality of removing such impurities is evident by the fact that the amount of these impurities is tested in final product (except viral load) and is part of final drug substance release specifications. All the chromatography samples including load, flow through, washes, and elution are analyzed using following analytical methods:

SDS PAGE (reduced/non reduced) for purity and single chain/double chain content.

Size Exclusion High performance Chromatography (SEC-HPLC) for aggregate content

TNK-tPA content measured by Clot Lysis assay.

Total Protein by Bradford and UV280 nm.

HCP content using ELISA (Cygnus third generation kit)

Example-4

The Affinity chromatography eluate without any conditioning is directly loaded on to cation exchange chromatography for concentration and buffer exchange of target protein. Cation exchange chromatography is optimized in such a way that it avoids cumbersome dilution steps for feed conditioning and therefore the affinity-III eluate can be directly loaded on to the cation exchange chromatography. TNK-tPA is recovered from the column by passing elution buffer containing 55 mg/ml L-Arginine, 17 mg/ml of orthophosphoric acid, 0.43 mg/ml Polysorbate 20 and pH 7.4. Cation exchange chromatography eluate is subjected to filtration for viral reduction and the resultant filtrate is further concentrated using Tangential Flow Filtration (TFF) system to achieve the final drug substance concentration. After concentration the TFF Retentate is sterile filtered and kept at −20° C. for further use. Drug substance produced by the purification process of present invention is thoroughly analyzed by the state of art and validated analytical procedures which includes but not limited to; Identity and purity check by SDS PAGE, Western Blot, N-terminal sequence analysis and peptide map, HCP determination using ELISA, Bioactivity and TNK-tPA quantification using clot lysis assay, Host cell DNA quantification using qPCR, Endotoxin quantification using LAL test, Aggregate and single chain/double chain content using size exclusion HPLC, Arginine content & Osmolality, Sialic acid, neutral sugars, type-I and type-II glycoforms analysis, Analysis of process related impurities e.g. Gentamycin, MTX, Urea, Sodium Caprylate, and EACA using in-house developed methods.

After extensive analysis and biophysical comparison with innovator product it can be concluded that the product purified by the process described in current invention is yielding TNK-tPA product which is highly similar to innovator product with overall process yield of more than 60%.

Example 5

A Periodic counter current chromatography (PCC) for affinity-I step has been performed with cell culture supernatant containing TNK-tPA from perfusion based bioreactor. In batch mode dynamic binding capacity for affinity-I chromatography media were evaluated and based on the information obtained from break through analysis a three column PCC has been experimented on XK16-5 ml BLUE SEPAHROSE FF. The chromatographic buffer compositions were kept same as mentioned in Example-1.

Example 6

The method for preparation of a liquid mixture of controlled pH & ionic strength for required buffers, dilution and/or conditioning of chromatography load by five pump based customized AKTA process system with a maximum flow rate of 600 L/h for TNK-tPA downstream processing. The liquid mixtures prepared with the above system with defined recipes are suitable for purification of TNK-tPA at different chromatography stages as mentioned in Example-1 to 4.

We claim:

1. A process for isolation and purification of TNK-tPA comprising steps of:
   (i) subjecting cell free harvest obtained from CHO cell culture to affinity chromatography to capture TNK-tPA and obtaining an eluate containing partially purified TNK-tPA;
   wherein the affinity chromatography comprises Blue Sepharose 6 FF as a stationary phase and a mobile phase, wherein the mobile phase is a mixture of sodium phosphate buffer, sodium chloride and urea;
   (ii) subjecting the eluate of step (i) to affinity chromatography for additional purification of TNK-tPA and obtain an eluate containing primarily TNK-tPA;
   wherein the affinity chromatography comprises Lysine Hyper D as a stationary phase and a mobile phase, wherein the mobile phase is a mixture of sodium acetate buffer, urea and epsilon aminocarproic acid (EACA);
   (iii) viral inactivation of eluate of step (ii) to obtain the viral inactivated sample;
   wherein viral inactivation is conducted by low pH and chemical inactivation, wherein chemical inactivation is done by treating the sample with sodium caprylate in the presence of urea;
   (iv) subjecting the viral inactivated sample of step (iii) to a further affinity chromatography-III for additional purification to obtain an eluate containing primarily highly purified TNK-tPA;
   wherein the affinity chromatography comprises is Ceramic Hydroxy Apatite (CHT) as a stationary phase and a mobile phase, wherein the mobile phase is a mixture of phosphate buffer, 2-(N-Morpholino) ethane-sulfonic acid hydrate (MES-Hydrate), sodium chloride and urea;
   (v) subjecting the eluate of step (iv) to cation exchange chromatography to obtain an eluate containing highly purified preparation of TNK-tPA;
   wherein the affinity chromatography comprises is Ceramic Hydroxy Apatite (CHT) as a stationary phase and a mobile phase, wherein the mobile phase is a mixture of phosphate buffer, 2-(N-Morpholino) ethane-sulfonic acid hydrate (MES-Hydrate), sodium chloride and urea;
   (vi) subjecting the eluate of step (v) to virus reduction filtration for removal of virus present;
   wherein virus filtration is carried out by PES nanofilter having a size in a range from 15-20 nm; and,
   (vii) concentrating the sample of step (vi) to obtain TNK-tPA;
   wherein the yield of the process is more than 60% and purity of TNK-tPA obtained is more than 95% as measured by Size exclusion chromatography.

2. The process as claimed in claim 1, wherein the TNK-tPA purity is more than 95% by Size Exclusion Chromatography and wherein the other critical quality attributes are:

| SDS PAGE | No additional band other than principal band observed |

-continued

| | |
|---|---|
| Monomer (%) | More than 95% |
| Single Chain Content (%) | More than 60% |
| HCP (ppm) | Less than 100 |
| HCD (ng/dose) | Less than 10. |

3. The process as claimed in step (i) of claim 1, wherein the sodium phosphate is present in range from 20-40 mM, sodium chloride is present in range from 1.5-2 M and urea is present in range from 2-3 M;
   wherein the pH of the mobile phase is present in range from 7.2-7.4.

4. The process as claimed in claim 3, wherein the affinity chromatography provides 0.8-1.5 log reduction in host cell proteins (HCP).

5. The process as claimed in step (ii) of claim 1, wherein the sodium acetate is present in range from 5-15 mM, urea is present in range from 2-3 M and EACA is present in range from 0.1-0.2 mM;
   wherein the pH of the affinity chromatography mobile phase is in range of pH 4.5-5.

6. The process as claimed in claim 5, wherein the affinity chromatography results 1-1.5 log reduction in host cell proteins (HCP) and 1-4 log reduction of viral clearance.

7. The process as claimed in claim 5, wherein the affinity chromatography results more than 1.5 log reduction with XMuLV and more than 4 log reduction with PRV.

8. The process as claimed in step (iii) of claim 1, wherein sodium caprylate is present in the range from 0.01%-0.07% (w/v), preferably in the range of 0.05%;
   wherein concentration of urea is present in the range of 2-3 M;
   wherein viral inactivation is conducted by holding the sample for a period from 40-80 minutes;
   wherein holding of the sample at a temperature range from 20-30° C.;
   wherein the pH is present in range from 4.3 to 4.7.

9. The process as claimed in claim 8, wherein the Low pH and chemical inactivation results in more than 5 log reduction with XMuLV and PRV.

10. The process as claimed in step (iv) of claim 1, wherein the phosphate buffer is present in range from 5-15 mM, MES-Hydrate is present in range from 2-20 mM, urea is present in range from 1-3 M and sodium chloride is present in range from 0.1 to 0.5 M;
    wherein the mobile phase pH is in the range from 6-9;
    wherein the affinity chromatography elution type is linear salt gradient;
    wherein the salt of this elution is sodium chloride in a range from 0.1-1.0 M sodium chloride.

11. The process as claimed in claim 10, wherein the affinity chromatography results 0.5-1 log reduction in host cell proteins (HCP) and 2-4 log of viral clearance.

12. The process as claimed in claim 10, wherein the affinity chromatography results more than 4 log reduction with XMuLV and PRV and more than 3 log reduction with MMV and Reo 3 viruses.

13. The process as claimed in step (v) of claim 1, wherein the L-Arginine is present in range from 250-350 mM, O-phosphoric acid is present in range from 0.6%-0.8% and polysorbate-20 is present in range from 0.04 to 0.05%; and,
    wherein the mobile phase pH is in range from 7.3-7.5.

14. The process as claimed in claim 13, wherein the cation exchange chromatography results more than 1 log viral clearance with MMV and more than 0.5 log clearance for host cell proteins (HCP).

15. The process as claimed in step (vi) of claim 1, wherein the virus filtration results more than 4 log reduction of XMuLV, more than 3 log reduction of PRV, more than 4 log reduction of Reo-3 and more than 4.5 log reduction of MMV.

16. The process as claimed in step (vii) of claim 1, wherein the filter is ultra filtration membrane;
    wherein the ultra filtration membrane is PES;
    wherein the size of ultra filtration membrane is in a range from 5-30 kDa, preferably the size of ultra filtration membrane is 10 kDa.

17. The process as claimed in claim 16, wherein the concentrate is TNK-tPA retentate.

* * * * *